US010234433B2

(12) United States Patent
Satzinger et al.

(10) Patent No.: US 10,234,433 B2
(45) Date of Patent: Mar. 19, 2019

(54) SAMPLING DEVICE AT HIGH PRECISION AND HIGH PRESSURE UTILIZING TWO DRIVES

(71) Applicant: DIONEX SOFTRON GMBH, Germering (DE)

(72) Inventors: Adolf Satzinger, Olching (DE); Hermann Hochgraeber, Offenberg-Neuhausen (DE); Thomas Armin Alexander Eichorn, Munich (DE)

(73) Assignee: Dionex Softron GmbH, Germering (DE)

( * ) Notice: Subject to any disclaimer, the term of this patent is extended or adjusted under 35 U.S.C. 154(b) by 412 days.

(21) Appl. No.: 14/534,027

(22) Filed: Nov. 5, 2014

(65) Prior Publication Data

US 2015/0128685 A1 May 14, 2015

(30) Foreign Application Priority Data

Nov. 8, 2013 (DE) .......... 10 2013 112 287

(51) Int. Cl.
*G01N 30/20* (2006.01)
*G01N 35/10* (2006.01)
*F04B 13/00* (2006.01)
*G01N 30/22* (2006.01)

(52) U.S. Cl.
CPC ............ *G01N 30/20* (2013.01); *F04B 13/00* (2013.01); *G01N 30/22* (2013.01); *G01N 2030/207* (2013.01)

(58) Field of Classification Search
CPC ........ G01N 2030/207; G01N 2001/065; F04B 9/047; F04B 9/103; F04B 9/1035; F04B 9/105; F04B 9/1053; F04B 9/1056; F04B 9/107

See application file for complete search history.

(56) References Cited

U.S. PATENT DOCUMENTS

| | | | |
|---|---|---|---|
| 3,922,115 A | 11/1975 | Coe et al. | |
| 4,003,679 A | 1/1977 | McManigill | |
| 4,722,675 A * | 2/1988 | Albarda ................. | F04B 9/047 417/509 |
| 8,806,922 B2 | 8/2014 | Hochgraeber | |
| 2008/0101970 A1* | 5/2008 | Witt ..................... | F04B 11/0075 417/521 |
| 2008/0199556 A1* | 8/2008 | Dantlgraber ........ | B29C 45/4005 425/542 |
| 2012/0003104 A1* | 1/2012 | Mueller ................ | F04B 9/02 417/53 |
| 2013/0064693 A1* | 3/2013 | Tschanz ............... | F04B 19/006 417/319 |

FOREIGN PATENT DOCUMENTS

CN 101644242 A 2/2010

\* cited by examiner

*Primary Examiner* — Leslie J Evanisko
*Assistant Examiner* — Quang X Nguyen

(57) ABSTRACT

The invention relates to a sampler for providing a sample for high-performance liquid chromatography, in which a volume of liquid to be taken up into a cylinder can be aspirated by means of a first drive and can be compressed to a high pressure level by means of a second drive independent of the first drive or can be decompressed from this level in a controlled manner.

19 Claims, 2 Drawing Sheets

SAMPLING DEVICE AT HIGH PRECISION AND HIGH PRESSURE UTILIZING TWO DRIVES

CROSS REFERENCE TO RELATED APPLICATIONS

This application claims the priority benefit under 35 U.S.C. § 119 to German Patent Application No. 10 2013 112 287.6, by Thomas Armin Alexander Eichhorn, Adolf Satzinger, and Hermann Hochgraeber for "Sampling device" filed on Nov. 8, 2013, the disclosure of which is incorporated herein by reference.

FIELD OF THE INVENTION

The present invention relates to a sampler and to a method for collecting a sample, in particular for uses in liquid chromatography.

BACKGROUND

In high-performance liquid chromatography, samples to be examined are fed into a high-pressure stream of liquid in order to be delivered to a chromatography column for analysis. For this purpose, a precisely defined amount of the sample is made available by being aspirated into a line (suction line), which forms part of what is called a sample loop. The line contains a solvent and is connected at a first end to a cylinder in which some of the solvent can be aspirated from the line by means of a piston. The other, second end of the line is immersed in a sample vessel prior to the aspiration. The volume of the solvent taken up on aspiration by the cylinder at the first end of the line corresponds to the volume of the sample aspirated at the second end of the line. By precise positioning of the piston, a precisely defined sample volume can thus be taken up into the line or the sample loop. After aspiration of the sample, further solvent can, if necessary, also be aspirated at the second end of the line, such that the sample is present as a "plug" in the line, enclosed on both sides by solvent.

Thereafter, the line is connected with its second end to a port through which the sample is intended to be conveyed out of the sample loop into a chromatography column. For this purpose, either the cylinder is integrated, together with the attached suction line, into the circulation of the solvent, or its content is conveyed back into the suction line via a branch line.

In the following, "sample loop" is to be understood as at least the content of said line and of the volume aspirated into the cylinder.

At first, the sample is generally at ambient pressure during the aspiration. However, the chromatography method is performed at very high pressure (>100 MPa), for which purpose a special pump is provided which forces the solvent as carrier medium through the chromatography column. To be able to feed the sample from the sample loop into the high-pressure column, the sample loop is integrated via a suitable valve into the delivery path after the aspiration and thereby conveyed to the chromatography column. So that the solvent provided in the sample loop volume can be brought together with the sample to the necessary high system pressure (thereby avoiding sharp fluctuations in pressure when the sample loop is switched in), the volume in the cylinder is compressed with the aid of the piston to approximately the expected operating pressure. The switching of the valve for injecting the sample into the chromatography column then takes place without pressure fluctuations and permits substantially stationary operation of the plant. To convey the sample out of the sample loop, it is possible, by switching the valve, to integrate the cylinder into the delivery path such that it flows through the latter. Alternatively, the piston can also drive the compressed volume actively into the line. Details of this method can be found in particular in DE 10 2008 006 266 B4, the disclosure of which is intended to be incorporated here in full.

If the sample loop is adapted to the high system pressure before being integrated by valve switching into the delivery path to the chromatography column, this affords in particular the advantages that the column does not experience any abrupt and possibly damaging pressure surges, and that the retention times remain constant (reproducibility). This is achieved if the sample loop is already brought to system pressure before switching on.

In this method, the piston of the sampler is on the one hand moved in order to aspirate a very precisely defined sample volume (of the order of microliters), while on the other hand it is subjected to very strong forces during the pre-compression of the sample loop to the operating pressure. The drive moving the piston thus has to meet very strict requirements both as regards the precision of the piston stroke and also as regards the strength of its components during the pre-compression. On account of the high forces during the pre-compression, larger and more robust components are needed, but this also leads to poorer reproducibility in the provision of the precise sample volume. Moreover, the spindle of the drive, designed for the high-precision positioning of the piston, is subjected to a considerable load during the pre-compression, which results in wear, abrasion and poorer precision. It has not hitherto been possible to provide different configurations of the drive that would ensure both the necessary precision and also the required strength.

SUMMARY

The object of the invention was therefore to propose a device and a method with which a sample volume can be made available both with very precise dosing and also at very high pressure.

The invention is based on the recognition that, in order to satisfy the two aims mentioned above, it is possible to use two mutually independent drives, of which one achieves the aim of high-precision dosing and the other achieves the aim of pre-compression. Each of the two drives can be configured to meet its special requirements, each drive being able to be coupled alternately to the piston of the cylinder in order to perform, with the latter, the collection of the sample or the pre-compression of the sample loop. The particular advantage is that the drive used to take up or aspirate a precisely defined sample volume can comprise high-precision components that would suffer damage if subjected to system pressure. Conversely, the other drive, which is less concerned with the reproducibility and precision of the piston positioning to provide an exact sample volume and more concerned with mechanical strength, can contain components that specifically meet these requirements. The needs of the respective other drive need not be taken into account, such that both requirements of the sampler can be optimally satisfied independently of each other. It is thus possible, for example, to safely avoid a situation where the drive (metering drive) determining the sample volume is exposed to piston forces that are generated during the pre-compression by the other drive (compression drive). Conversely, the compression drive is not involved in the piston movements that are caused by the metering drive. The functional separation of the two drives from each other is effected by mechanical decoupling of the respectively unused drive from the piston acted upon by both drives.

Drives "independent of each other" are to be understood as drives that each contain dedicated drive components that are not used in the operation of the respective other drive. Each drive can in principle be coupled to and uncoupled from the piston independently of the respective other drive, preferably mechanically. However, a common control can be provided for both drives. Moreover, boundary conditions can occur during operation, in which case one drive or the control suppresses or blocks functions of the other drive (end positions, overload, etc.).

The sampler according to the invention is designed for collecting and dispensing a sample volume, as is necessary in particular in liquid chromatography. The sampler comprises a cylinder, with a piston movable in the latter. In order to collect a defined volume of solvent in the cylinder, the piston is movable along a cylinder axis Z. According to the invention, two drives independent of each other are provided, which are designed for different tasks and so introduce different piston forces into the piston. The metering drive $D_M$ serves for the high-precision positioning of the piston in the cylinder, so as to be able to aspirate a precisely defined sample volume into the sample loop. This is generally done at ambient pressure, such that the metering drive can be designed only for relatively low actuating forces on the piston. By contrast, the compression drive is able to subject the piston to high forces, so as to be able to subject the cylinder and the sample loop to pressures in excess of 100 MPa. Preferably, both drives act on a common piston from the same side, for example via a piston rod of the piston.

For this purpose, they can be alternately coupled to/uncoupled from the piston by means of a higher-level control, such that the drive responsible for the respective function (aspiration or compression, or conveying or decompression) engages on the piston, while the other drive is uncoupled from the piston or is able to follow the movements of the piston at least without interfering counterforces.

To be able to couple both drives to the piston, each drive is assigned coupling means which transmit the force of the respective drive to the piston. In an advantageous embodiment of the invention, the coupling means extend concentrically with respect to each other in at least one section. For example, a spindle of the compression drive, designed as a hollow tube, could guide a movable pin in its interior and along its longitudinal axis, which pin can be acted upon by the metering drive. At one end, the spindle of the compression drive, here serving as the coupling means of the compression drive, can act in the axial direction on the piston, or on a connecting piece connected thereto, when the spindle abuts this. In a screwed back position, in which the spindle of the compression drive does not act on the piston, the pin (as coupling means of the metering drive) guided in the spindle can instead act axially on the piston or on the connecting piece when the pin is moved back sufficiently through the spindle to the piston.

The concentric arrangement of the coupling means, which also preferably extend concentrically with respect to the cylinder axis Z, allows a space-saving construction and reduces the demands associated with the mounting of the piston and of the piston rod. In order also to avoid asymmetrical loading of the components involved in the sampling or conveying or pre-compression or decompression, central engagement of the compression drive components or metering components on the piston is recommended.

According to an advantageous embodiment of the invention, the piston is urged into a retracted position by permanently acting tensioning means, from which position it can be moved when acted upon by the metering drive or the compression drive. The influence of production tolerances or of a resulting play in a drive is reduced by the tensioning means. For example, the flanks of a spindle nut and of its spindle are always pressed against each other as a result of the pretensioning of the tensioning means, without allowing production-related axial play between spindle and nut during a reversal of movement. This is advantageous particularly for the precision of the metering drive, which can have such a spindle with spindle nut. Since, on account of the permanent tensioning means, the piston always moves in one direction "by itself", the metering drive can move the piston in both directions by purely acting on the pressure (increasing or reducing an axial shearing force). A tensioning of the piston is then not necessary, and corresponding hysteresis effects upon the reversal of movement of the piston do not occur in the spindle drive.

To meet demands in high-performance liquid chromatography, the compression drive is preferably configured such that it can generate pressure forces of over 100 MPa in the cylinder. For this purpose, the compression drive can have a stationary toothed belt pulley configured as a spindle nut. With a suitable pinion on the shaft of a motor, the latter drives the toothed belt pulley via a toothed belt, as a result of which a spindle rotationally fixed in the center of the toothed belt pulley and arranged on the Z axis is driven in an axial forward movement. The spindle can act on the piston directly or via additional coupling means. By virtue of the relationship of the radii between spindle and toothed belt pulley or between the latter and the pinion of the motor, suitable gear ratios can be established in order to subject the piston to the force necessary for the pre-compression.

The metering drive can also have a spindle with spindle nut, said spindle preferably being arranged in a stationary and rotationally fixed manner on a housing of the sampler and being flush with the cylinder axis Z. A spindle nut sitting on the stationary spindle can be screwed along the longitudinal axis thereof in the Z direction by rotation about the spindle and can be coupled to the piston directly or via additional coupling means. At the same time, the spindle nut of the metering drive is configured as a toothed belt pulley and is connected by a toothed belt to a matching pinion of a motor of the metering drive. Since the toothed belt pulley of the metering drive moves in the axial direction during its rotation about the spindle, the toothed belt also travels along with it on the pinion of the stationary motor of the metering drive. In this way, means for mounting the spindle nut are advantageously dispensed with, as a result of which the imprecision associated with said mounting is also avoided.

As a result of a slight pitch of the spindle or spindle nut and a high transmission from the motor to the spindle nut, the axial forward movement of the latter can be set very precisely. The metering drive is preferably configured such that the sample volume to be taken up in the cylinder can be set with a reproducible accuracy of at least 0.1 µl. Particularly preferably, the accuracy even lies in the range below 0.01 µl.

The inventive separation of the functions of the sampler between two independent drives serves, among other things, to protect the high-precision components of the metering drive from excessive loads during operation. In order to ensure this protection even when the sampler is used incorrectly, a preferred embodiment of the invention provides an overload safeguard, which avoids an inadvertently high degree of loading of the components of the metering drive. It is achieved by the fact that, in the event of an overload, a coupling between the metering drive, on the one hand, and the piston or coupling means interacting therewith, on the other hand, is separated axially (flush with the piston axis). This can entail coupling means, which are arranged concentrically with respect to the cylinder axis and which connect the metering drive to the piston, executing a movement relative to each other when a predefinable axial shearing force is exceeded, as a result of which a connection transferring shearing force between the spindle nut of the metering drive and a coupling means is released. High forces, with which the piston or the coupling means coupled thereto are pushed further in the direction of the spindle nut, are then no longer transferred to the spindle nut, and the coupling means engage as it were in a void.

A particularly expedient embodiment of this overload safeguard comprises a magnet which engages in the interior of a spindle nut and which is connected in a shear-resistant manner to the coupling means. The magnet sits on an inner surface of the spindle nut directed away from the piston, wherein the coupling means (e.g. in the form of a pin) connected to the magnet lead centrally out of the spindle nut to the piston. If the shearing force (pressure in the cylinder+ pre-tensioning force of the tensioning means+friction) exerted on the spindle nut of the metering drive by the piston exceeds the holding force of the magnet, the latter detaches itself from the inner surface of the spindle nut, as a result of which the latter is decoupled from the piston and, therefore, from the load that has become too great. It cannot therefore sustain damage.

In order to bring the two drives alternately into engagement with the piston, the respective motors drive the spindle nuts such that the spindle of the compression drive engages with or disengages from the piston or a connecting piece attached thereto. The same applies to the metering drive, in which the spindle nut, or a coupling means coupled thereto, engages on or is lifted away from the piston or a connecting piece connected thereto. In the coupling and uncoupling of the metering drive to and from the piston or the connecting piece, it is important, for the reproducibility of the aspirated volume, to produce a form-fit connection of the parts to be separated from each other or connected to each other, said form-fit connection being reproducible within narrow tolerances. Since at least in the above-described embodiment the spindle of the metering drive also rotates, and therefore also the coupling means connected thereto, this rotation movement about the Z axis also has to be taken up on the rotationally fixed piston.

According to an advantageous embodiment of the invention, provision is made for use of a pin which leads concentrically from the metering drive through the spindle of the compression drive and which, at its front end, can be moved with a form fit against a connecting piece of the piston or can be lifted away therefrom. In the force flow between pin and connecting piece, a ball is arranged on the Z axis, on which ball the pin centers itself with a centering surface worked into its front end. The pin can be produced from steel or brass, while the ball is made of, for example, ceramic, ruby or hardened steel. The ball permits the centering of the pin in a relatively simple way, for example in a central bore of the connecting piece, which bore contains the ball. The ball centers itself on the conical bottom surface of the bore, as is present in the case of a blind bore. A suitable conical front face of the pin, or a front face otherwise adapted to the ball shape, centers itself, upon contact with the opposite side of the ball, automatically with respect to the axis of the bore, which for its part is flush with the cylinder axis. Asymmetrical loading of the piston by the metering drive is thereby prevented, as also are undefined contact conditions between pin and connecting piece or piston, thus promoting the desired reproducibility. At the same time, the material pairing permits a low-wear rotation movement of the pin in relation to the rotationally fixed ball.

The method according to the invention for providing a sample volume comprises, in analogy to the above embodiments, at least the following steps:

a) aspirating the sample volume with the aid of a cylinder configured about an axis Z, for which purpose a first drive drives a piston arranged movably in the cylinder;

b) acting on the piston via a second drive independent of the first drive, in order to build up a predeterminable pressure in the cylinder or to reduce this pressure in a controlled manner.

Here, "reduce [ . . . ] in a controlled manner" means lowering the pressure, with constant control, from a high level to a lower pressure, preferably ambient pressure.

The piston is preferably moved in a first direction during the aspiration by means of the metering drive, which can be effected by permanently acting tensioning means. In the pressure build-up by means of the compression drive, the piston is acted upon in the opposite direction. The drives expediently act on the piston via coupling means that extend concentrically with respect to each other, the drives being alternately controlled in such a way that one drive acts on the piston while the other is uncoupled from the piston. Only at the change-over of function (pre-compression of the aspirated volume) is it possible for both drives to be briefly engaged with the piston, if the compression drive uncoupled for the sampling is actuated such that it "takes over" the piston from the metering drive and compresses the aspirated volume. Only from the advance movement of the compression drive or by additional rearward movement of the metering drive does the latter disengage from the piston.

BRIEF DESCRIPTION OF THE DRAWINGS

An embodiment of a sampler according to the invention will be explained in more detail below on the basis of an example in the figures.

DETAILED DESCRIPTION OF EMBODIMENTS

Figure 1:
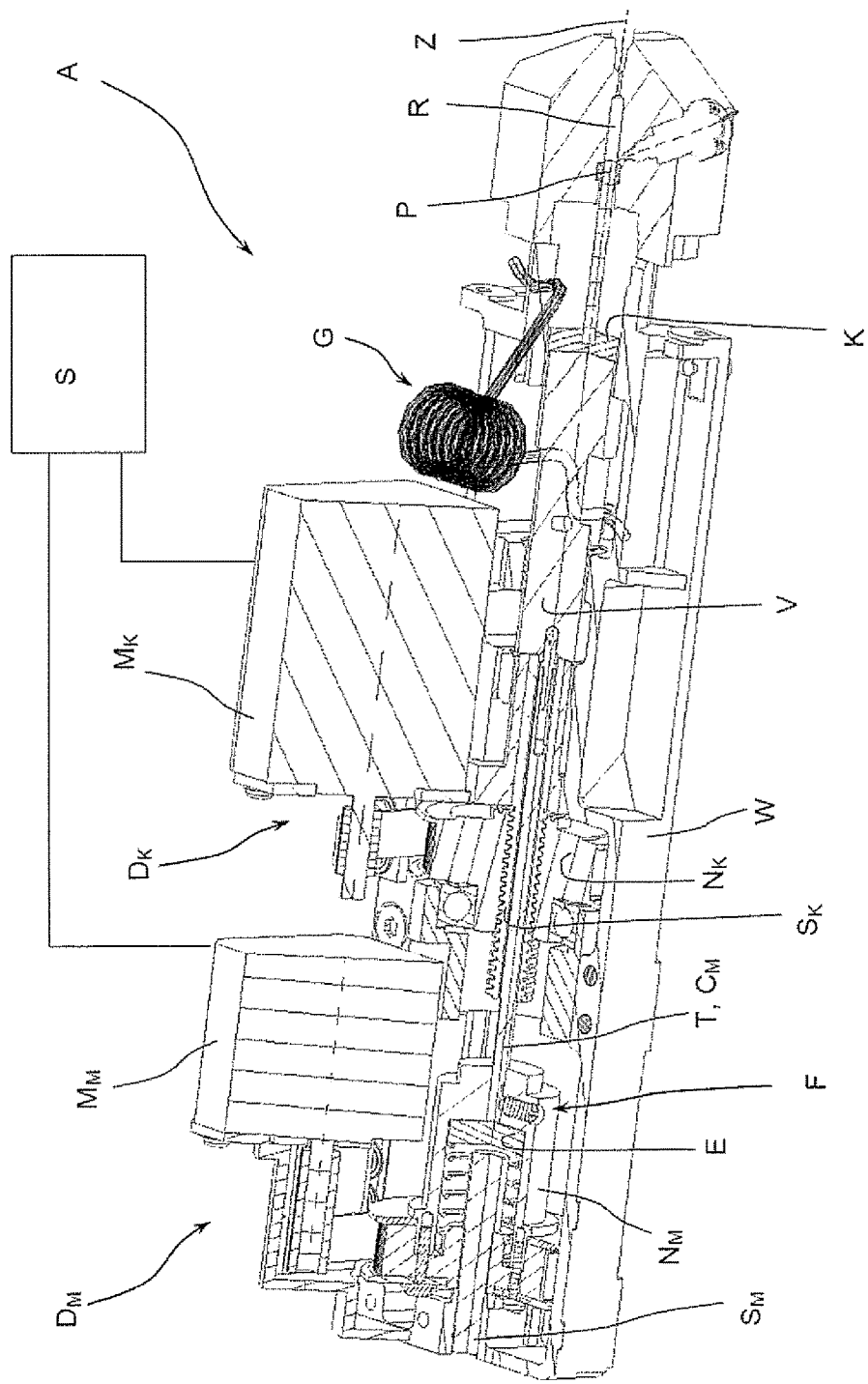
FIG. 1 shows a perspective view of a sampler according to the invention.

The sampler A shown in FIG. 1 comprises a frame structure W, which extends substantially along an axis Z. At one end (the right-hand end in FIG. 1), the frame structure W is provided with an attachment which, in its interior, comprises a cylinder R configured to be rotationally symmetrical with respect to the Z axis. A piston P is movable to and fro in the cylinder R in the Z direction. A connecting part V acts on the piston P in the Z direction via a piston plate K. For this purpose, the connecting piece V is mounted movably in the Z direction on the frame structure W. A tensioning means configured as a helical spring G acts on the connecting part V with a pretensioning force, which urges the connecting part V, the piston plate K connected thereto and, therefore, the piston P into a retracted position, toward the left in FIG. 1.

A motor $M_K$, which belongs to a compression drive $D_K$, is arranged on the frame structure W. By way of a toothed belt, the motor engages with its pinion on a toothed belt pulley $N_K$, which is arranged on the frame structure W in a fixed position but is rotatable about the axis Z. The toothed belt pulley $N_K$ comprises a spindle nut, which guides a rotationally fixed spindle $S_K$ centrally. By rotation of the toothed belt pulley $N_K$, the spindle $S_K$ is caused to perform an axial movement in the Z direction relative to the toothed belt pulley $N_K$. In so doing, it moves toward the connecting piece V or away from the latter, such that the compression drive $D_K$ can alternately act on the piston P or be uncoupled therefrom.

The frame structure W carries a further motor $M_M$, which is part of a metering drive $D_M$. A toothed belt driven on the shaft of the motor $M_M$ via a pinion drives a toothed belt pulley $N_M$, which is at the same time configured as a spindle nut. The toothed belt pulley $N_M$ screws its way along a spindle $S_M$ arranged in a stationary position, concentrically with respect to the Z axis, and fixed in rotation on the frame structure W when it is moved in rotation by the motor $M_M$. In a forward movement of the toothed belt pulley $N_M$ in the Z direction, the toothed belt accordingly travels too on the pinion of the motor $M_M$.

On its side facing the piston P, a pin T protrudes from the toothed belt pulley $N_M$ in the direction of the piston P and extends concentrically with respect to the Z axis through the spindle $S_K$ of the compression drive $D_K$. With its front end (the right-hand end in FIG. 1), the pin T, which follows an axial advance of the rotating toothed belt pulley $N_M$, is able to act on the connecting piece V and thus the piston P. A rotation of the toothed belt pulley $N_M$ in the opposite direction has the effect that the pin T is lifted away from or uncoupled from the connecting part V, such that the metering drive $D_M$ then no longer acts on the piston P.

Elements serving to transfer force to the piston P from one of the two motors $M_K$, $M_M$ can also be designated as coupling elements $C_K$ and $C_M$, respectively, depending on whether they serve the metering drive ($D_M$) or the compression drive ($D_K$).

At its rear end (the left-hand end in FIG. 1), the pin T is connected to a magnet E arranged in the interior of the toothed belt pulley $N_M$. The magnet E sits on an inner surface of the toothed belt pulley $N_M$ directed away from the piston P and, when its magnetic holding force is overcome, can lift away from this surface and move farther toward the left in the Z direction by a predefinable distance. The toothed belt pulley $N_M$ then no longer follows this movement. The magnet E forms part of an overload safeguard F, with which excessive forces on the components of the metering drive are avoided. If the piston P were to act with a force above a defined limit value on the pin T via the connecting part V and also on the toothed belt pulley $N_M$ via the magnetic connection, the magnet E is dimensioned in terms of its holding force in such a way that it detaches itself from the inner surface of the toothed belt pulley $N_M$ and thus decouples the axial shear from the piston P on the metering drive $D_K$.

Provision of a sample volume using the sampler according to the invention takes place as follows:

By way of a suction line connected to the cylinder R and not shown in any detail in FIG. 1, a defined volume of a solvent fluidically coupled to a sample volume is aspirated into the cylinder R by pulling the piston P back from an advanced position. For this purpose, the metering drive $D_M$ is controlled such that the toothed belt pulley $N_M$ functioning as spindle nut is moved toward the left in FIG. 1. In this way, the pin T can also move toward the left. The connecting part V pretensioned toward the left by the spring G follows this movement and likewise pulls the piston P toward the left via the piston plate K. As a result of the then increasing volume in the cylinder R, a corresponding amount of the solvent, typically provided at ambient pressure, is aspirated into the cylinder R. Along with the solvent aspirated from the line into the cylinder, a corresponding amount of a sample is at the same time aspirated from a sample vessel, to which the lower end of the line is connected, into the line or sample loop. In the sample loop, which includes at least the volume aspirated into the cylinder and the volume of the suction line, solvent is thus present with a precisely defined sample volume.

To collect the sample volume, the spindle $S_K$ of the compression drive $D_K$ has been driven so far to the left, by actuation of the toothed belt pulley $N_K$, that the front end (the right-hand end in FIG. 1) of the spindle $S_K$ does not collide with the connecting part V during the entire piston stroke. The very precise metering drive $D_M$ can aspirate a very precisely definable volume of solvent into the cylinder R, for which purpose the motor $M_M$ is controlled by the higher-level control S. The sample volume aspirated into the line can be determined with corresponding precision. For simplicity, any sensors with which the axial position of the piston P or the rotation position of the toothed belt pulley $N_M$ could be determined for checking the aspirated volume are not shown here.

The aspirated liquid in the sample loop is then intended to be compressed to a high pressure, for which purpose the free end of the suction line is coupled pressure-tight to a (still closed) injection port. The motor $M_K$ of the compression drive $D_K$ is then triggered by the control S to drive the toothed belt pulley $N_K$, in order to move the spindle $S_K$ in the Z direction toward the connecting part V and to engage the latter. In this way, the compression drive $D_K$ is coupled to the piston P and, by further advance of the spindle $S_K$, the sample in the cylinder R can be brought to the desired pressure, wherein the compression drive $D_K$ with its spindle $S_K$ moves the connecting part V against the pretensioning force of the spring G and in particular against the pressure force building up in the cylinder R. Pressure sensors for monitoring the internal pressure of the cylinder, which sensors can be connected to the control S, are not shown.

As a result of the forward movement of the connecting part V in the pre-compression, the pin T disengages from the connecting part V, and the metering drive $D_M$ is uncoupled from the piston P. After the desired target pressure in the cylinder R or in the sample loop is reached, the port is opened, and the sample compressed together with the solvent can be delivered to an attached chromatography column, as is described at the outset.

Conversely, the volume locked in the cylinder R (after completion of the chromatography) can be returned to ambient pressure (decompression), by means of the compression drive $D_K$ driving the spindle $S_K$ in the opposite direction. The connecting part V will follow this movement, which is driven by the spring G and the overpressure still present in the cylinder R. As long as the pin T is not coupled to the connecting part V, only the compression drive $D_K$ takes up the forces acting on the connecting part V, and the metering drive $D_M$ is not loaded. If appropriate, the control S can screw the toothed belt pulley $N_M$ of the metering drive $D_M$ so far to the left on the spindle $S_M$ that the contact between the pin T and the connecting part V is safely excluded until the ambient pressure that is safe for the metering drive D has established itself in the cylinder R.

By subsequent forward movement of the pin T via the metering drive D, the piston P can be moved to a forward, precisely defined starting position, so as to expel the residual volume from the cylinder R and then to be able to aspirate a new sample volume.

Figure 2:
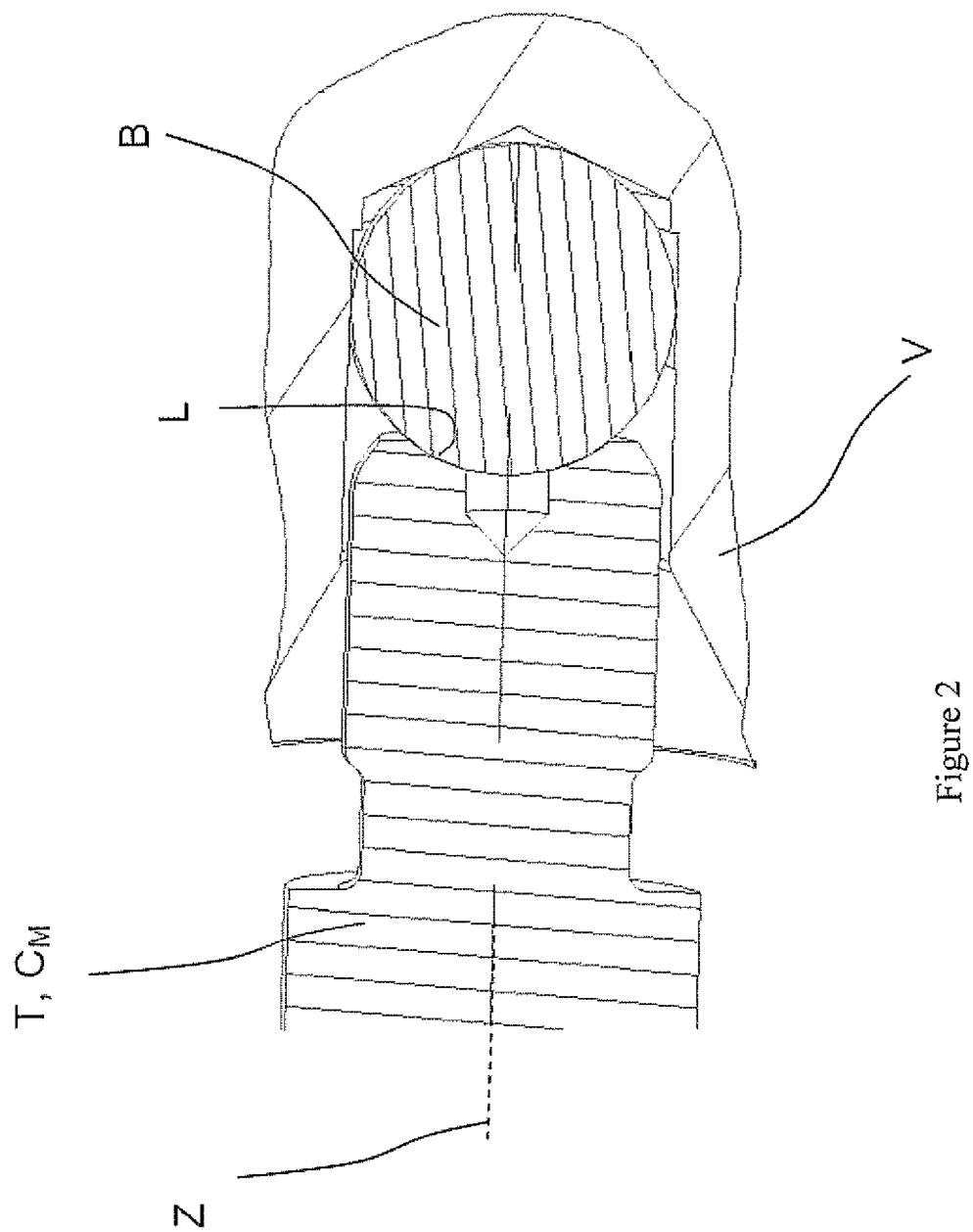
FIG. 2 shows a detail of the coupling area between metering drive and piston.

FIG. 2 shows a detail of the coupling area in which the pin T abuts the connecting part V when the metering drive $D_M$ is intended to actuate the piston P. A bore is formed on the side of the connecting part V facing toward the pin T, the bore axis being flush with the cylinder axis Z. A ball B is introduced into the bore and centers itself with respect to the Z axis on the conically tapering working surfaces in the bore base. On its side facing toward the bore opening, the ball is acted on by the front end of the pin T via a contact surface L. The contact surface L has centering portions, with the aid of which the pin is able to orient itself or center itself on the ball such that the axis of the pin T runs through the center point of the ball B.

As can be seen from FIG. 1, the pin T extending in the interior of the spindle $S_K$ is arranged with its rear end in the toothed belt pulley $N_M$ and is centered there with respect to the Z axis. When the pin T bears on the ball B shown in FIG. 2, the front end of the pin T is also oriented on the Z axis. Asymmetrical loading of the connecting part V or of the piston P by the metering drive is thereby avoided. In addition, the material pairing between the ball and the front end of the pin T serves as a slide bearing, since the pin T held in the toothed belt pulley $N_M$ rotates about the Z axis, while it is moved axially by the metering drive $D_M$. In addition to the centering, the ball B therefore also permits the choice of a suitable material pairing of pin T/ball B, which minimizes the friction and in particular the degree of wear, so as to be able to precisely set the stroke of the piston P with the metering drive $D_M$ in a reproducible manner.

What is claimed is:

1. A sampling device for collecting and dispensing a sample volume for liquid chromatography, the sampling device comprising:
   a) a piston in a cylinder,
   b) the piston configured to be movable along a cylinder axis to collect the sample volume in the cylinder, and
   c) two drives configured to generate different piston forces on the piston, in which the two drives are independent of each other, each drive is configured to be coupled to and uncoupled from the piston independently of a respective other drive,
   wherein the two drives each include respective coupling means, the coupling means each configured to transfer a force of the respective drive to the piston, and the respective coupling means extend concentrically with respect to each other and to the cylinder axis in at least one section,
   wherein a second drive of the two drives is configured as a compression drive to generate pressure forces of over 100 MPa in the cylinder,
   wherein a first drive of the two drives is configured as a metering drive to aspirate the sample volume into the cylinder,
   wherein the metering drive comprises an axially movable toothed belt pulley configured as a spindle nut of the metering drive where the spindle nut of the metering drive is screwed along a stationary spindle to transfer a drive force to the piston, and
   wherein the coupling means of the metering drive engages on the spindle nut of the metering drive via a magnet, the magnet arranged in an interior of the spindle nut of the metering drive, the magnet is configured to detach from the spindle nut of the metering drive in an axial direction along the cylinder axis when a shearing force exerted on the spindle nut of the metering drive exceeds a holding force of the magnet.

2. The sampling device as claimed in claim 1, wherein the coupling means of the metering drive comprises a pin arranged concentrically with respect to the cylinder axis, in which the pin transfers force from the metering drive to the piston with a ball, the ball being disposed between the pin and the piston.

3. The sampling device as claimed in claim 2, wherein the spindle of the compression drive is a hollow tube where the hollow tube guides the pin.

4. A sampling device for collecting and dispensing a sample volume for liquid chromatography, the sampling device comprising:
   a piston reciprocally movable within a cylinder along a cylinder axis,
   a first metering drive controlling movement of the piston in a first direction along the cylinder axis to collect the sample volume within the cylinder, and
   a second compression drive controlling movement of the piston in a second opposite direction along the cylinder axis to bring the cylinder to a desired pressure,
   in which the first metering drive is mechanically uncoupled from the second compression drive while the first metering drive controls piston movement, and the second compression drive is mechanically uncoupled from the first metering drive while the second compression drive controls piston movement,
   whereby the first metering drive imparts actuating forces on the piston to collect the sample volume, and the second compression drive imparts compression forces on the piston to bring the cylinder to the desired pressure, wherein the actuating forces are lower than the compression forces.

5. The sampling device as claimed in claim 4, wherein the first metering drive and the second compression drive each include respective first and second coupling means configured to engage the piston, and the respective coupling means extend concentrically with respect to each other and to the cylinder axis.

6. The sampling device as claimed in claim 5, wherein the first coupling means is a pin extending through the second coupling means.

7. The sampling device as claimed in claim 4, wherein the piston is not subjected to the actuating forces while the second compression drive subjects the piston to the compression forces, and the piston is not subjected to the compression forces while the first metering drive subjects the piston to the actuating forces.

8. The sampling device as claimed in claim 7, wherein the actuating forces allow collection of the sample volume at ambient pressure and the compression forces subject the cylinder to pressures in excess of 100 MPa.

9. A sampling device for collecting and dispensing a sample volume for liquid chromatography, the sampling device comprising:
   a piston reciprocally movable within a cylinder along a cylinder axis,
   a first metering drive controlling movement of the piston in a first direction along the cylinder axis to collect the sample volume within the cylinder, and
   a second compression drive controlling movement of the piston in a second opposite direction along the cylinder axis to bring the cylinder to a desired pressure, in which the second compression drive is mechanically uncoupled from the piston while the first metering drive controls piston movement, and the first metering drive is mechanically uncoupled from the piston while the second compression drive controls piston movement.

10. The sampling device as claimed in claim 9, wherein each of the first and second drives include respective coupling means configured to transfer a force of the respective drive to the piston, and the respective coupling means extend concentrically with respect to each other and to the cylinder axis in at least one section.

11. The sampling device as claimed in claim 10, wherein the first metering drive applies a force to the piston along the cylinder axis, the first metering drive is configured with an overload safeguard to axially separate a coupling between the first metering drive and the coupling means of the first metering drive.

12. The sampling device as claimed in claim 9, wherein the piston is urged into a retracted position by a tensioning means.

13. The sampling device as claimed in claim 12, in which the tensioning means comprises a spring.

14. The sampling device as claimed in claim 9, wherein the second compression drive is configured to generate pressure forces of over 100 MPa in the cylinder.

15. The sampling device as claimed in claim 14, wherein the second compression drive is also configured to reduce pressure.

16. The sampling device as claimed in claim 14, wherein the second compression drive comprises a stationary toothed belt pulley configured as a spindle nut of the compression drive to transfer a drive force to a spindle axially movable in a center of the spindle nut of the second compression drive, in which the spindle applies force to the piston.

17. The sampling device as claimed in claim 16, in which the spindle applies force to the piston via a connecting piece.

18. The sampling device as claimed in claim 9, wherein the first metering drive comprises an axially movable toothed belt pulley configured as a spindle nut of the metering drive where the spindle nut of the metering drive is screwed along a stationary spindle to transfer a drive force to the piston.

19. The sampling device as claimed in claim 9, wherein the first metering drive applies a force to the piston along the cylinder axis, the first metering drive is configured with an overload safeguard to axially separate a coupling between the metering drive and the piston.

* * * * *

UNITED STATES PATENT AND TRADEMARK OFFICE
CERTIFICATE OF CORRECTION

PATENT NO. : 10,234,433 B2
APPLICATION NO. : 14/534027
DATED : March 19, 2019
INVENTOR(S) : Adolf Satzinger et al.

Page 1 of 1

It is certified that error appears in the above-identified patent and that said Letters Patent is hereby corrected as shown below:

On the Title Page

Item (72), Line 4, Inventors:
Replace "Eichorn,"
With --Eichhorn,--

Signed and Sealed this
Twenty-fourth Day of September, 2019

Andrei Iancu
*Director of the United States Patent and Trademark Office*